United States Patent [19]

Dick et al.

[11] Patent Number: 4,624,567

[45] Date of Patent: Nov. 25, 1986

[54] FLUID PARTICLE SENSOR

[75] Inventors: Scott M. Dick, Alta Loma; Edward F. Patterson, Redlands, both of Calif.

[73] Assignee: Wehr Corporation, Milwaukee, Wis.

[21] Appl. No.: 599,007

[22] Filed: Apr. 11, 1984

[51] Int. Cl.[4] ............................................. G01N 15/02
[52] U.S. Cl. ..................................... 356/335; 356/442
[58] Field of Search ....................... 356/335, 441, 442; 250/564, 573, 576, 227

[56] References Cited

U.S. PATENT DOCUMENTS 3,864,044 2/1975 Lyshkow ..................... 250/573 X
3,924,951 12/1975 Dittrich ............................. 356/335

Primary Examiner—Davis L. Willis
Assistant Examiner—Matthew W. Koren

[57] ABSTRACT

A fluid particle sensor for measuring and counting particles contained in a fluid. The fluid particle sensor comprises a first bundle of generally parallel elongated fiber optics, the first bundle having a longitudinal axis and opposite inside and outside ends, and a second bundle of generally parallel elongated fiber optics, the second bundle also having a longitudinal axis and opposite inside and outside ends. The sensor also comprises means for supporting the first and second bundles such that the longitudinal axes of the first and second bundles are approximately colinear, and such that the inside end of the second bundle is closely spaced apart from the inside end of the first bundle to form a gap through which the particle containing fluid flows. The sensor further comprises means for transmitting light to the outside end of the first bundle, and means for sensing the amount of light emitted from the outside end of the second bundle.

16 Claims, 4 Drawing Figures

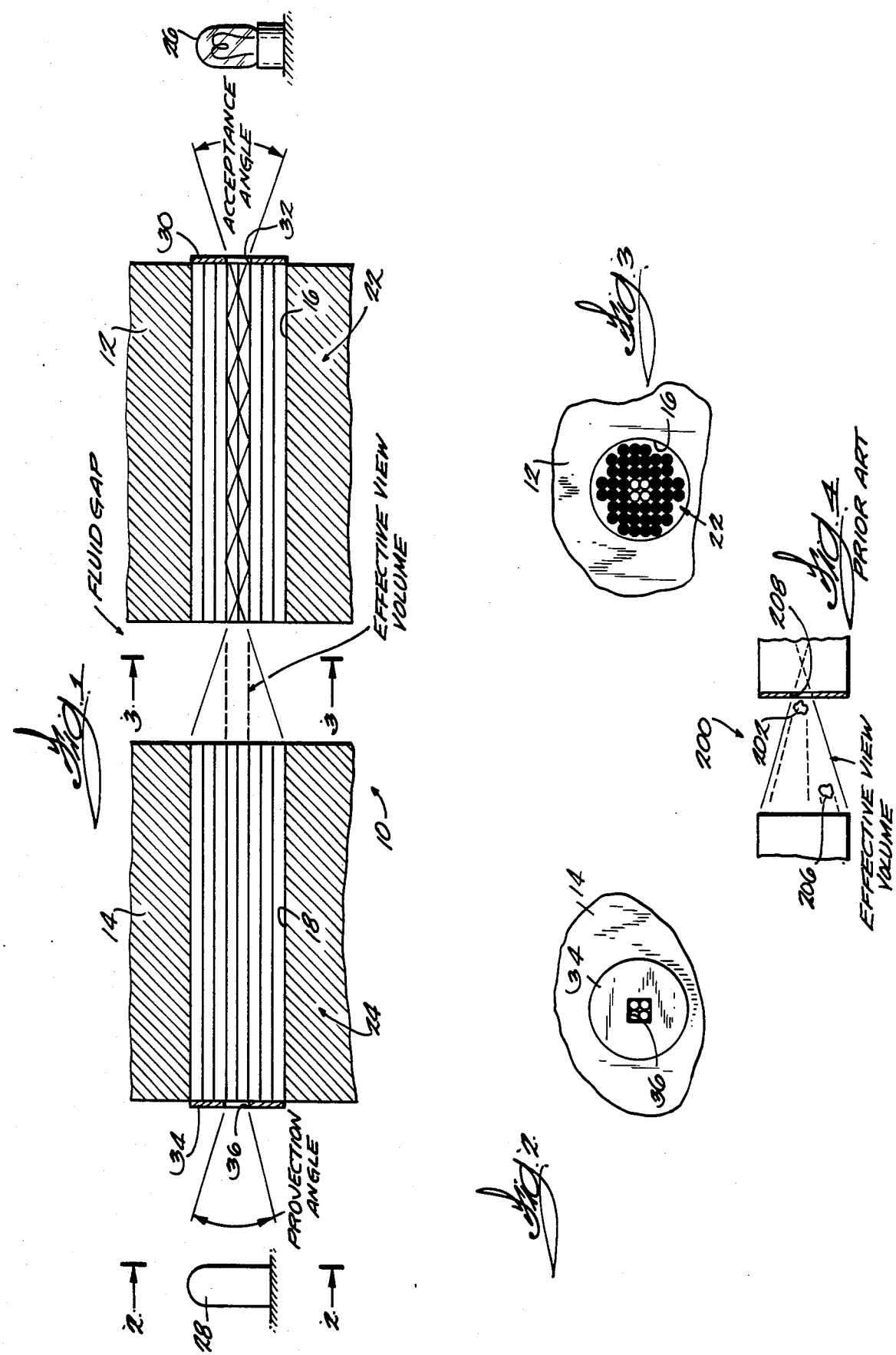

FLUID PARTICLE SENSOR

FIELD OF THE INVENTION

The invention relates to sensors for measuring and counting particles contained in a fluid, and more particularly to such sensors of the "blockage" or "obscuration" type.

BACKGROUND OF THE INVENTION

Prior blockage type fluid particle sensors comprise two stainless steel blocks having closely spaced apart planar surfaces forming a fluid gap, typically 1000 microns across, through which the fluid that is to be analyzed flows. Each block has a bore therethrough, the bores having a common longitudinal axis perpendicular to the planar surfaces, and each bore contains a transparent rod having inside and outside ends, with the inside end of each rod being aligned with the planar surface of the stainless steel block that holds the rod, so that the inside ends of the rods are separated by the fluid gap. One of the rods, hereinafter the masked rod, is covered on both ends by a pair of mask plates having identical aligned rectangular apertures. A light source is located adjacent the outside end of the masked rod, and an optical detector system is located adjacent the outside end of the other rod, hereinafter the unmasked rod.

Light rays from the light source enter the masked rod through the aperture in the mask plate covering the outside end of the masked rod. The size of the aperture is typically 150 microns across. The light rays are reflected by the inner walls of the masked rod until they exit through the aperture in the mask plate covering the inside end of the rod. The light rays then cross the fluid gap between the blocks and enter the inside end of the unmasked rod, pass through the rod, and exit the outside end of the unmasked rod, where they are detected by the optical detector system.

Particles in the fluid passing through the fluid gap block some of the light rays, thereby creating a shadow which is sensed by the optical detector system.

A problem with these prior blockage-type fluid particle sensors is that the optical detector system can be fooled. Since the optical detector system sees only shadows and not the actual particles in the fluid, the size of a particle as measured by the optical detector system depends on the size of the shadow cast by the particle, and the number of particles in the fluid as measured by the optical detector system depends on the number of individual shadows cast by the particles in the fluid.

To create a shadow, a particle must be within the view volume of the sensor, i.e., the volume that is illuminated by the light rays passing from the masked rod to the unmasked rod through the gap.

The effective view volume of prior sensors is a truncated pyramid having as its small end the aperture at the inside end of the masked rod, and having as its base the inside end of the unmasked rod. Because of the shape of this effective view volume, a particle near the unmasked rod creates a much larger shadow than a particle near the unmasked rod, so that a particle near the masked rod will be sensed as being much larger than the same particle near the unmasked rod. Sizing errors can be as great as 20:1.

Also, because of the large size of the effective view volume of prior sensors, the maximum number of particles per unit volume of fluid that can accurately be counted is approximately 5,555 particles per millimeter.

The larger the view volume, the smaller the number of particles per unit volume of fluid that can be accurately counted. This is because an accurate count, irrespective of the size of the particles, is only achieved when only one particle at a time is present in the view volume. The detector cannot distinguish between the light blockage or shadows of two particles in the view volume at the same time, so it will yield an electrical signal response equal to one apparently larger particle when this condition occurs. Decreasing the size of the view volume decreases the probability of two particles being in the view volume at the same time. Thus, decreasing the size of the view volume increases the number of particles per unit volume of fluid that can be accurately counted.

Of course, the view volume of a prior sensor can be reduced in size simply by reducing the mechanical proportions of the sensor, but this presents the problems of increased operational pressure requirements, reduced sample flow rates, and flow blockage due to plugging of the microscopic sensing zone by the particles to be measured and counted. Furthermore, such a reduction of the proportions of a prior sensor will not change the shape of the view volume, a truncated pyramid, so that sizing errors will still result.

It has been recognized by the inventor of this application that the optimum view volume is a rectangular solid extending across the fluid gap and having a cross section that equals the area of the aperture in the mask plate covering the inside end of the masked rod. This view volume is optimal partly because of its shape. A particle therein casts approximately the same shadow when it is near the unmasked rod as when it is near the masked rod. This view volume is also optimal because it is the smallest obtainable view volume, so that counting errors are minimized.

This optimum view volume can only be obtained if an extremely well collimated beam of light is transmitted through the aperture at the outside end of the masked rod, and this is very difficult, if not impossible, on this small scale (150 microns) with current technology.

Another problem that causes both sizing errors and counting errors is that stray light that reaches the optical detector system will affect particle sensing. Stray light can reach the optical detector system, for instance, by entering the inside end of the unmasked rod or the outside end of the masked rod and being transmitted through the rod or rods to the optical detector system. Stray light entering the rods at almost any angle will eventually be transmitted to the optical detector system.

Another problem with prior sensors is that the apertures at the opposite ends of the masked rod must be perfectly aligned to maximize energy through-put and to minimize the effective view volume.

SUMMARY OF THE INVENTION

The invention provides a fluid particle sensor for measuring and counting particles contained in a fluid. In the preferred embodiment, the fluid particle sensor comprises first and second bundles of generally parallel elongated fiber optics. Each fiber optic has a longitudinal axis and opposite end surfaces transverse to the longitudinal axis. Each fiber optic transmits light along its length, with light rays being able to enter a fiber optic only through an end surface and only within a predetermined acceptance angle. Light rays exit a fiber optic only through the end surface opposite the end surface of entry, and only within a predetermined projection angle.

The bundles of fiber optics each have a longitudinal axis and opposite inside and outside ends, and the longitudinal axis of the first bundle is approximately colinear with the longitudinal axis of the second bundle. The inside end of the first bundle is closely spaced apart from the inside end of the second bundle, such that the first and second bundles are closely spaced apart along the longitudinal axis to form a gap through which the particle containing fluid flows. The fluid particle sensor also comprises means for transmitting light to the outside end of the first bundle, and means for sensing the amount of light emitted from the outside end of the second bundle.

In the preferred embodiment, the first and second bundles are contained in bores through first and second stainless steel blocks. The first block has a planar surface and a bore therethrough, the bore having a longitudinal axis perpendicular to the planar surface and containing the first bundle such that the inside end of the first bundle is aligned with the first block planar surface. The second block has a planar surface and a bore therethrough, the second block planar surface being parallel to and closely spaced apart from the first block planar surface to further form the gap for the particle containing fluid to pass through. The second block bore has a longitudinal axis perpendicular to the second block planar surface and contains the second bundle such that the inside end of the second bundle is aligned with the second block planar surface.

Preferably, the fluid particle sensor further comprises a first mask plate abutting and covering the outside end of the first bundle, and a second mask plate abutting and covering the outside end of the second bundle. The first mask plate includes a first aperture therein such that light is transmitted from the light transmitting means to at least one of, but not all of, the fiber optics at the outside end of the first bundle, and the second mask plate includes a second aperture which is the same size as the first aperture and which allows light to be emitted from at least one of, but not all of, the fiber optics at the outside end of the second bundle to the light sensing means. In the preferred embodiment, the first and second apertures measure approximately 150 microns across.

Furthermore, the light transmitting means of the fluid particle sensor is preferably a light, and the light sensing means is preferably an optical detector system.

One advantage of the fluid particle sensor of the invention is that it provides the optimum view volume. Because of the shape of the view volume of the sensor, a particle will create a shadow of only one size regardless of its location in the view volume. Therefore, sizing errors are essentially eliminated. Because of the size of the view volume, the number of particles per unit volume of fluid that can accurately be counted is greatly increased. The maximum particle concentration that can be accurately measured by the fluid particle sensor of the invention is approximately eight times greater than the maximum particle concentration that can be measured by prior sensors.

Another advantage of the fluid particle sensor of the invention is that it can analyze fluids that are much dirtier than the dirtiest fluids that can be measured with prior sensors, without the need to drastically reduce the mechanical proportions of the sensor. This avoids the problems of increased operational pressure requirements, greatly reduced sample flow rates, and flow blockage due to plugging of the microscope sensing zone by the particles to be measured and counted.

Another advantage of the fluid particle sensor of the invention is that the apertures at the outside ends of the fiber optic bundles need not be perfectly aligned.

Another advantage of the fluid particle sensor of the invention is that the fiber optics concentrate the light entering the first aperture into the view volume.

Another advantage of the fluid particle sensor of the invention is that stray light, or light coming from outside the acceptance angle of the fiber optics, will not be transmitted to the optical detector system.

Other advantages of the invention will become apparent to those skilled in the art upon review of the following detailed description, claims, and drawings.

DESCRIPTION OF THE DRAWINGS

FIG. 1 is a cross-sectional view of the fluid particle sensor of the invention.

FIG. 2 is an end view taken along line 2—2 in FIG. 1.

FIG. 3 is an end view of the first bundle of fiber optics taken along line 3—3 in FIG. 1.

FIG. 4 is an enlarged cross-sectional view of the sensing zone of a prior art fluid particle sensor.

Before explaining one embodiment of the invention in detail, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

Shown in FIG. 4 is the effective view volume of a prior art fluid particle sensor 200. As previously discussed under Background of the Invention, this effective view volume creates several problems. The two major problems are sizing errors and counting errors. The counting errors result in a limited maximum particle concentration that can be accurately counted. Furthermore, reducing the mechanical proportions of a prior art fluid particle sensor in order to increase the maximum particle concentration that can be accurately counted results in further problems which include increased operational pressure requirements, reduced sample flow rates, and flow blockage due to plugging of the microscopic sensing zone by the particles to be measured and counted.

Sizing errors result from the pyramid shape of the effective view volume of the prior art fluid particle sensor. As shown in FIG. 4, a particle 202 near the aperture 208 of the prior art sensor 200 will cast a larger shadow than a particle 206 that is farther away from the aperture 208, so that the particle 202 nearer the aperture will be sensed as being much larger than the other particle 206.

Counting errors result from the relatively large size of the view volume of prior art sensors. Counting errors occur because the optical detector system senses the shadow or reduced light as though only one particle is within the view volume when in fact two particles are within the view volume at one time. Since increasing the size of the view volume increases the likelihood of having two particles in the view volume at one time, the large prior art view volume leads to an increased likelihood of counting errors. For instance, in the situation illustrated in FIG. 4, the optical detector system of the prior art sensor 200 would detect only one particle, although two are present within the view volume. Furthermore, it can be seen that if a third particle were present in the shadow of particle 202, the third particle would not be detected at all.

Both sizing and counting errors also result from stray light reaching the optical detector system, because stray light causes "false" light sensing.

Illustrated in FIG. 1 is the fluid particle sensor 10 of the invention. Stainless steel blocks 12 and 14 are closely spaced apart in order to form a fluid gap (shown in FIG. 1). Each of the blocks 12 and 14 has a bore 16 and 18, respectively, therethrough, with each bore having a longitudinal axis perpendicular to the parallel planar surfaces forming the fluid gap. Ideally, the bores 16 and 18 have a common longitudinal axis, but unlike with prior art sensors, the longitudinal axes need only be approximately colinear.

In the preferred embodiment, each of the bores 16 and 18 contains a bundle of generally parallel elongated fiber optics, with the first bundle 22 of fiber optics being contained in the bore 16 in the first block 12, and the second bundle 24 of fiber optics being contained in the bore 18 in the second block 14. Each bundle of fiber optics has an inside end and an outside end, and the inside ends of the bundles 22 and 24 are aligned with the planar surfaces forming the fluid gap so that the inside ends are on opposite sides of the fluid gap.

Adjacent the outside end of the first bundle 22 of fiber optics is a light source 26, and adjacent the outside end of the second bundle 24 of fiber optics is an optical detector system 28. Light emitted by the light source 26 passes through the first bundle 22 of fiber optics, through the fluid gap (unless blocked by a particle), and through the second bundle 24 of fiber optics, from which it is transmitted to the optical detector system 28.

Each fiber optic has a longitudinal axis and opposite end surfaces transverse to the longitudinal axis. Each fiber optic transmits light along its length, with light rays being able to enter a fiber optic only through an end surface and only within a predetermined acceptance angle. Light rays exit a fiber optic only through the end surface opposite the end surface of entry, and only within a predetermined projection angle.

The fiber optic acceptance and projection angles are shown in FIG. 1. Due to the acceptance angle, it is difficult for stray light to enter a fiber optic. As a general rule, only light from the light source enters 26 the fiber optics of the first bundle 22, and only light emitted from the first bundle enters the second bundle 24 and is transmitted to the optical detector system 28. Thus, sizing and counting errors caused by stray light are essentially eliminated. The limited projection angle provides the benefits of less stray light within the fluid gap and concentration of light within the view volume.

Covering the outside end of the first bundle 22 of fiber optics is a first mask plate 30. The first mask plate has therein a small aperture 32, preferably approximately 150 microns across and rectangular, which allows light to be transmitted from the light source to at least one, but not all, of the fiber optics of the first bundle 22. Covering the outside end of the second bundle 24 of fiber optics is a second mask plate 34. The second mask plate has therein a small aperture 36, which is the same size as the aperture 32, and which allows light to be emitted toward the optical detector system 28 from at least one, but not all, of the fiber optics of the second bundle 24. The apertures 32 and 36 need not be perfectly aligned.

Due to the nature of fiber optics, as explained previously, the aperture 32 at the outside end of the first bundle 22 of fiber optics effectively defines the illuminated area on both ends of the first bundle 22. In other words, the aperture 32 determines the number and position of the individual fibers to be "activated" by the light source 26. Only those fibers uncovered by the aperture 32 and not covered by the mask plate 30 are activated. All other fibers are shielded from the light source 26 by the first mask plate 30 and, therefore, remain dark throughout their length. FIG. 3 shows the effect of the aperture 32, viewing from the inside end of the first bundle 22 of fiber optics. For purposes of illustration, only four fibers are shown within the area of the aperture 32, although an array of up to 900 fibers within a 150 micron square is easily possible with current fiber optic technology.

In the same manner, the aperture 36 at the outside end of the second bundle 24 of fiber optics determines the number and position of the activated fibers in the second bundle 24. Only those fibers uncovered by the aperture 36 and not covered by the mask plate 34 are activated. All other fibers in the second bundle 24 are shielded from the optical detector system 28 by the second mask plate 34, so that they cannot transmit light to the optical detector system 28. FIG. 2 is an end view of the fluid particle sensor 10 showing the activated fibers of the second bundle 24 exposed by the aperture 36 at the outside end of the second bundle 24. Again, only four fibers are shown for purposes of illustration.

Because only the fibers uncovered by the aperture 36 at the outside end of the second bundle 24 can transmit light to the optical detector system 28, only light received by those same fibers at the inside end of the second bundle 24 can be transmitted to the optical detector system 28. Since the aperture 32 at the outside end of the first bundle 22 determines which fibers of the first bundle 22 transmit light to the fibers of the second bundle 24, the effective view volume of the fluid particle sensor is determined by the apertures 32 and 36 at the outside ends of the bundles 22 and 24. The effective view volume is, in the preferred embodiment, a rectangular solid having as one end the activated fibers at the inside end of the first bundle 22, and as the other end the activated fibers at the inside end of the second bundle 24. This is illustrated in FIG. 1.

The effective view volume of the fluid particle sensor 10 is also the optimum view volume. As a result, sizing errors are essentially eliminated, and counting errors are minimized, so that the number of particles per unit volume of fluid that can be measured is maximized.

Sizing errors are eliminated because identically sized particles in the view volume cast identically sized shadows regardless of their proximity to the first bundle 22 of fiber optics. This occurs because the light rays in the effective view volume of the sensor 10 are effectively parallel, since they are transmitted essentially straight across the fluid gap, unlike the light rays of the prior art sensor 200.

Counting errors are minimized because the size of the view volume is minimized, and thus the likelihood of having two particles in the view volume at once is minimized. Because counting errors are minimized, the fluid particle sensor 10 can analyze fluids that are much dirtier than the dirtiest fluids that can be analyzed with prior sensors.

Various other features of the invention are set forth in the following claims.

We claim:

1. A fluid particle sensor for measuring and counting particles contained in a fluid, said fluid particle sensor comprising a first bundle of generally parallel elongated light transmitting members, said first bundle of light transmitting members having a longitudinal axis and opposite inside and outside ends, said members each having a longitudinal axis and opposite end surfaces transverse to said longitudinal axis, and each of said members transmitting light along the length thereof, with light rays being able to enter said members only through said end surfaces and only within a predetermined acceptance angle measured from said longitudinal axis, and with light rays being able to exit said members only through the end surface opposite the end surface through which the light rays entered and only within a predetermined projection angle measured from said longitudinal axis, a second bundle of generally parallel elongated light transmitting members, said second bundle having a longitudinal axis and opposite inside and outside ends, means for supporting said first and second bundles such that the longitudinal axes of said first and second bundles are approximately colinear, and such that said inside end of said second bundle is closely spaced apart from said inside end of said first bundle to form a gap through which the particle containing fluid flows, means for transmitting light to said outside end of said first bundle, means for sensing the amount of light emitted from said outside end of said second bundle, a first mask plate abutting and covering said outside end of said first bundle, said first mask plate including a first aperture such that light is transmitted from said light transmitting means to at least one of, but not all of, said member at said otuside end of said first bundle, and a second mask plate abutting and covering said outside end of said second bundle, said second mask plate including a second aperture which is the same size as said first aperture and such that light is emitted from at least one of, but not all of, said members at said outside end of said second bundle to said light sensing means.

2. A fluid particle sensor as set forth in claim 1 wherein said first and second apertures measure approximately 150 microns across.

3. A fluid particle sensor for measuring and counting particles contained in a fluid, said fluid particle sensor comprising a first bundle of generally parallel elongated fiber optics, said first bundle having a longitudinal axis and opposite inside and outside ends, a second bundle of generally parallel elongated fiber optics, said second bundle having a longitudinal axis and opposite inside and outside ends, means for supporting said first and second bundles such that the longitudinal axes of said first and second bundles are approximately colinear, and such that said inside end of said second bundle is closely spaced apart from said inside end of said first bundle to form a gap through which the particle containing fluid flows, means for transmitting light to said outside end of said first bundle, means for sensing the amount of light emitted from said outside end of said second bundle, first means for causing light to be transmitted at said inside end of said first bundle only from a first group of said fiber optics of said first bundle, said first group having a cross-sectional area and including at least one of, but not all of, said fiber optics of said first bundle, and second means for causing light to be transmitted at said outside end of said second bundle only from a second group of said fiber optics of said second bundle, said second group having the same cross-sectional area as said first group and including some of, but not all of, said fiber optics of said second bundle.

4. A fluid particle sensor as set forth in claim 3 wherein said light transmitting means is a light and wherein said light sensing means is an optical detector system.

5. A fluid particle sensor as set forth in claim 3 wherein said means for supporting said first and second bundles comprises a first block having a planar surface and a bore through said first block, said first block bore having a longitudinal axis perpendicular to said first block planar surface and containing said first bundle such that said inside end of said first bundle is aligned with said first block planar surface, and a second block having a planar surface and a bore through said second block, said second block planar surface being parallel to and closely spaced apart from said first block planar surface to further form the gap for the particle containing fluid to pass through, said second block bore having a longitudinal axis perpendicular to said second block planar surface and containing said second bundle such that said inside end of said second bundle is aligned with said second block planar surface.

6. A fluid particle sensor as set forth in claim 5 wherein said first means includes a first mask plate abutting and covering said outside end of said first bundle, said first mask plate including a first aperture therein such that light is transmitted from said light transmitting means to at least one of, but not all of, said fiber optics at said outside end of said first bundle, and wherein said second means includes a second mask plate abutting and covering said outside end of said second bundle, said second mask plate including a second aperture which is the same size as said first aperture and such that light is emitted from at least one of, but not all of, said fiber optics at said outside and of said second bundle to said light sensing means.

7. A fluid particle sensor as set forth in claim 5 wherein said light transmitting means is a light and wherein said light sensing means is an optical detector system.

8. A fluid particle sensor as set forth in claim 3 wherein said first means includes means for causing light to be transmitted at said outside end of said first bundle only to said first group of said fiber optics of said first bundle.

9. A fluid particle sensor as set forth in claim 8 wherein said first means includes a first mask plate abutting and covering said outside end of said first bundle, said first mask plate including therein a first aperture such that light is transmitted from said light transmitting means to at least one of, but not all of, said fiber optics at said outside end of said first bundle, and wherein said second means includes a second mask plate abutting and covering said outside end of said second bundle, said second mask plate including therein a second aperture which is the same size as said first aperture and such that light is emitted from at least one of, but not all of, said fiber optics at said outside end of said second bundle to said light sensing means.

10. A fluid particle sensor as set forth in claim 9 wherein said first and second apertures measure approximately 150 microns across.

11. A fluid particle sensor as set forth in claim 3 wherein said first means includes a first mask plate abutting and covering one of said ends of said first bundle, said first mask plate including therein a first aperture such that light is transmitted into said gap from at least one of, but not all of, said fiber optics at said inside end of said first bundle, and wherein said second means includes a second mask plate abutting and covering one of said ends of said second bundle, said second mask plate including therein a second aperture which is the same size as said first aperture and such that light is emitted from at least one of, but not all of, said fiber optics at said outside end of said second bundle to said light sensing means.

12. A fluid particle sensor as set forth in claim 11 wherein said first and second apertures measure approximately 150 microns across.

13. A fluid particle sensor for measuring and counting particles contained in a fluid, said fluid particle sensor comprising a first bundle of generally parallel elongated fiber optics, said first bundle having a longitudinal axis and opposite inside and outside ends, a second bundle of generally parallel elongated fiber optics, said second bundle having a longitudinal axis and opposite inside and outside ends, means for supporting said first and second bundles such that the longitudinal axes of said first and second bundles are approximately colinear, and such that said inside end of said second bundle is closely spaced apart from said inside end of said first bundle to form a gap through which the particle containing fluid flows, means for transmitting light to said outside end of said first bundle, means for sensing the amount of light emitted from said outside end of said second bundle, a first mask plate abutting and covering said outside end of said first bundle, said first mask plate including a first aperture such that light is transmitted from said light transmitting means to at least one of, but not all of, said fiber optics at said outside end of said first bundle, and a second mask plate abutting and covering said outside end of said second bundle, said second mask plate including a second aperture which is the same size as said first aperture and such that light is emitted from at least one of, but not all of, said fiber optics at said outside end of said second bundle to said light sensing means.

14. A fluid particle sensor as set forth in claim 13 wherein said light transmitting means is a light and wherein said light sensing means is an optical detector system.

15. A fluid particle sensor as set forth in claim 13 wherein said first and second apertures measure approximately 150 microns across.

16. A fluid particle sensor for measuring and counting particles contained in a fluid, said fluid particle sensor comprising a first block having a planar surface and a bore through said first block, said first block bore having a longitudinal axis perpendicular to said first block planar surface, a first bundle of generally parallel elongated fiber optics, said first bundle having opposite inside and outside ends, and said first bundle being contained in said first block bore such that said inside end of said first bundle is aligned with said first block planar surface, means for transmitting light to said outside end of said first bundle, a first mask plate abutting and covering said outside end of said first bundle, said first mask plate including a first aperture therein such that light is transmitted from said light transmitting means to at least one of, but not all of, said fiber optics at said outside end of said first bundle, a second block having a planar surface and a bore through said second block, said second block planar surface being parallel to and closely spaced apart from said first block planar surface to form a gap for the particle containing fluid to pass through, said second block bore having a longitudinal axis perpendicular to said second block planar surface and approximately colinear with said first block bore longitudinal axis, a second bundle of generally parallel elongated fiber optics, said second bundle having opposite inside and outside ends, and said second bundle being contained in said second block bore such that said inside end of said second bundle is aligned with said second block planar surface, with said inside end of said second bundle being closely spaced apart from said inside end of said first bundle on opposite sides of the gap through which the particle containing fluid flows, a second mask plate abutting and covering said outside end of said second bundle, said second mask plate including a second aperture therein which is the same size as said first aperture and such that light is emitted from at least one of, but not all of, said fiber optics at said outside end of said second bundle through said second aperture, and means for sensing the amount of light emitted through said second aperture.

* * * * *